United States Patent [19]

Hirschberg et al.

[11] Patent Number: 5,342,413
[45] Date of Patent: Aug. 30, 1994

[54] MEDICAL ELECTRODE ARRANGEMENT

[75] Inventors: Jakub Hirschberg, Taeby; Heinz Neubauer, Jaerfaella; Nina Gilljam, Farsta; Staffan Bowald, Almunge; Ulf Lindegren, Enskede, all of Sweden

[73] Assignee: Siemens-Elema AB, Solna, Sweden

[21] Appl. No.: 63,555

[22] Filed: May 19, 1993

[30] Foreign Application Priority Data

May 21, 1992 [SE] Sweden ............................. 9201600

[51] Int. Cl.⁵ ............................................. A61N 1/05
[52] U.S. Cl. ................................. 607/126; 128/642
[58] Field of Search ............... 607/122, 123, 126, 127, 607/128, 129, 130, 131; 128/642

[56] References Cited

U.S. PATENT DOCUMENTS

| | | | |
|---|---|---|---|
| 3,737,579 | 6/1973 | Bolduc | 607/131 |
| 4,311,153 | 1/1982 | Smits | 607/127 |
| 4,355,642 | 10/1982 | Alferness | 128/642 |
| 4,357,946 | 11/1982 | Dutcher et al. | 607/131 |
| 4,463,765 | 8/1984 | Gold | 607/127 |
| 4,624,266 | 11/1986 | Kane | 607/131 |
| 4,922,927 | 5/1990 | Fine et al. | 607/122 |
| 4,972,847 | 11/1990 | Dutcher et al. | 607/131 |
| 5,005,587 | 4/1991 | Scott | 607/122 |
| 5,016,645 | 5/1991 | Williams et al. | 607/129 |
| 5,282,845 | 2/1994 | Bush et al. | 607/128 |

FOREIGN PATENT DOCUMENTS 0211166 2/1987 European Pat. Off. ............ 607/126

Primary Examiner—Angela D. Sykes
Assistant Examiner—George Manuel
Attorney, Agent, or Firm—Hill, Steadman & Simpson

[57] ABSTRACT

An electrode arrangement for in vivo stimulation of tissue with electrical energy has a catheter containing an electrical lead, the lead and the catheter being electrically and mechanically connected to further electrical conductors, arranged in a configuration forming a broad, flat, thin and flexible electrode. The conductors in the electrode are partially exposed and define an electrode surface for delivering electrical energy to adjacent tissue. The electrode arrangement further includes a fixing device, for attaching the electrode to tissue surrounding the tissue to be stimulated. The fixing device includes a fixing element which is mounted on the electrode so as to be movable independently of the electrode, and a stylet which controls movement of the fixing element, the stylet extending through the catheter. The fixing element can be controlled so as to be advanced from a retracted position to a position extending beyond the electrode surface in which the fixing element penetrates the tissue.

12 Claims, 2 Drawing Sheets

MEDICAL ELECTRODE ARRANGEMENT

BACKGROUND OF THE INVENTION

1. Field of the Invention

The present invention is directed to an electrode arrangement for a medical apparatus for in vivo stimulation of tissue with electrical energy, and in particular to an electrode arrangement of the type having a flat electrode with a large electrode area, which is electrically coupled to an electrode catheter lead, and having a fixing device for attaching the electrode to tissue.

2. Description of the Prior Art

A cardiac electrode arrangement is disclosed U.S. Pat. No. 4,355,642 which has a relatively thick disk-shaped base which supports a first electrode in the form of a spike, and a second electrode in the form of a helix, with a sharp tip, surrounding the spike. The electrode arrangement is affixed to the epicardium by screwing the entire disk-shaped base into the cardiac tissue, by rotation of the entire disk-shaped base until the flat surface of the base comes into contact with the epicardium. Electrical discharge occurs in the cardiac tissue between the tip of the helix and the tip of the spike. In another embodiment, a third electrode in the form of a ring is provided on the disk-shaped base, the ring surrounding the helix electrode.

In order for this known electrode device to be attached to the heart, the patient must undergo thoracic surgery, by which the chest is opened to expose the heart. The electrode can only be affixed to the exposed portion of the heart. Moreover, screwing the electrode into the heart is traumatic to heart tissue, and leads to the formation of scar tissue in the epicardium. Moreover, the electrode must be correctly situated before the screwing the helix into the epicardium since the electrode arrangement cannot be subsequently moved without damage to the heart tissue.

Moreover, since the disk-shaped base is relatively thick in relation to its area, the electrode arrangement is stiff, and therefore cannot conform to the exterior of the heart and is thus unable to assume a relatively large area enabling transmission of a pulse to the largest possible portion of the heart. Since the electrode arrangement is screwed into the epicardium by being rotated until the surface of the base element comes into contact with the heart tissue, the orientation of the electrode arrangement relative to the heart tissue is governed by the operation of screwing the electrode arrangement into the epicardium. The electrode arrangement must therefore have a rotationally symmetrical surface, at least in terms of its electrically conductive elements.

An epicardial pacing electrode is disclosed in U.S. Pat. No. 3,737,579 having an electrode catheter, with a helical electrode mounted at a right angle to the longitudinal axis of the catheter, and Dacron ® webbing disposed substantially perpendicularly to the longitudinal axis. With the aid of a special, substantially tubular tool, into which the pacing electrode arrangement is inserted with the helix pointing in the direction of the longitudinal axis of the tool, the helix can be screwed into the heart by rotating the tool until the Dacron ® webbing comes into contact with heart tissue. The electrode can be additionally affixed by suturing the Dacron ® webbing to the heart.

In this known device, the electrode area is small, as is standard for a pacing electrode, however, the device could not be modified to significantly increase the electrode area, because the electrode arrangement is screwed at a right angle into heart tissue. As a result of the fixed helix in this known pacing electrode, electrode fixing and orientation with respect to the heart are performed simultaneously. Orientation of the electrode arrangement thus arises directly from the fixing operation, so that the position of the electrode after the helix has been screwed into the heart tissue cannot be altered. This means that the electrode catheter could ultimately extend upwardly or downwardly after implantation, with the ultimate orientation of the catheter not being able to be determined in advance because that orientation is a function of the extent to which the helix is screwed into the cardiac tissue.

A defibrillator electrode arrangement is disclosed in European Patent 0 211 166 containing a plurality of individual electrodes. Each electrode has a fixing plate with a helix for affixing that electrode to the heart. The tip of the helix points at a right angle relative to the longitudinal axis of the catheter. A plurality of coiled conductors are disposed around the fixing plate, these conductors forming the active electrode surface. For implantation, a tool is used similar to that employed in the aforementioned U.S. Pat. No. 3,737,579. The tool is connected to the fixing plate with the helix oriented so that when the tool is rotated, the helix is screwed into the heart tissue until the surface of the fixing plate comes into contact with the heart. The coiled electrode conductors are, during implantation, raised from the fixing plate and are held along the exterior of the tool with needles respectively disposed at the ends of the coiled conductors. When the fixing plate is screwed into place, the coiled electrode conductors are detached from the tool, and are applied to the heart tissue and affixed thereto using the needles. After all of the electrodes have been attached to the heart, they are interconnected with a common electrode catheter.

In this known electrode arrangement, a plurality of electrodes is used to cover a large part of the heart tissue, thus making more comprehensive implantation surgery necessary. The large number of electrodes also results in a large number of lesions on the heart tissue, thereby increasing the risk of post-operative complications. Moreover, the electrodes must be symmetrical, for the same reason discussed above with regard to other known electrode arrangements. The fixing plate is stiff, and the direction of the electrode catheters in the implanted position cannot be determined in advance, thereby increasing the difficulty in interconnecting the individual electrode catheters to the common electrode catheter.

For endocardial electrode arrangements, the use of a movable helix for attaching an electrode to heart tissue is known. One such electrode arrangement is described in U.S. Pat. No. 4,311,153. During introduction into the heart, the helix is enclosed in a sleeve which constitutes a part of the electrode catheter so that no tissue is damaged. The sleeve is coated with a membrane to prevent the entry of body fluids. Inside the heart, the helix is advanced to affix the electrode to endocardial tissue. The helix is advanced in a direction along the longitudinal axis of the electrode catheter by rotation of a connection contact attached to the helix, or by means of a detachable stylet inside the electrode catheter.

Another known endocardial electrode arrangement is described in U.S. Pat. No. 4,922,927, and contains a defibrillation electrode extending the length of an electrode catheter, and a pacing electrode at the end of the electrode catheter. A movable helix is attached to the end of the catheter at which the pacing electrode is disposed. During implantation of the electrode arrangement, the helix can be manipulated with a stylet so it rotates around an axis parallel to the longitudinal axis of the electrode catheter, and can thereby be screwed into heart tissue for fixing the electrode arrangement. The electrode arrangement can be removed from the tissue if the screw is rotated in the opposite direction.

As noted, the axis of rotation of the helix in both of the above known endocardial electrode arrangements is parallel to the axis of the electrode catheter, so that the electrode devices can be pressed against heart tissue during implantation as the helix is screwed into the tissue, thereby ensuring a firm seating of the helix, even though the helix is remotely manipulated. The same result is obtained in the epicardial electrode arrangements for which a tool is employed for aiming the helix at the heart tissue and for rotating the entire electrode.

SUMMARY OF THE INVENTION

It is an object of the present invention to provide an electrode arrangement having an electrode surface for in vivo delivery of electrical energy to tissue, which, without extensive surgery, can be implanted, remotely manipulated, and repositioned a number of times.

The above object is achieved in accordance with the principles of the present invention in an electrode arrangement wherein the electrode is thin and flexible, and wherein the fixing device includes a fixing element which is movable independently of the electrode, the electrode catheter having a channel to hold a stylet for controlling the fixing element. The electrode has an electrode contact surface and the fixing element is controllable so that it can be advanced from a retracted position to a position extending beyond the contact surface against tissue in order to attach the electrode to the tissue.

As used herein, the term "electrode" refers to the overall structure which is attached to the distal end of the catheter (distal relative to a stimulation pulse generator attached at an opposite end of the catheter). Moreover, as used herein, the description of the electrode as being broad or covering a large area is intended to distinguish the disclosed electrode from known electrodes of the type described above, wherein the electrical contact between the electrode and the tissue takes place within a relatively small, confined point-like region, or between closely disposed points.

Because the electrode constructed in accordance with the principles of the present invention is thin and flexible, it can conform to the contours of the tissue to which it is to be attached, and because of the independently movable fixing element, a much larger electrode surface, or effective electrode surface, conforming to tissue contours can be achieved, because electrode placement and orientation is achieved separately from electrode fixing to the tissue. The fixing element can be easily advanced with the stylet to affix the electrode, or can be withdrawn if relocation or position adjustment is necessary. As a result of its flexibility, the electrode can be coiled and advanced against the tissue, for example, through an introducer catheter, thereby reducing the necessary scope of implantation surgery. The electrode can be moved using the stylet until it reaches the desired position, and can then be affixed. Because this operation is controlled from outside the patient in whom the electrode arrangement is to be implanted, the scope of surgery is reduced even further.

As noted above, in known electrode arrangements which have a movable helix, such as that disclosed in U.S. Pat. Nos. 4,311,153 and 4,922,927, the helix is advanced parallel to the electrode catheter. This would not be possible with the other types of known electrode devices described above, such as that in U.S. Pat. No. 4,355,642 and in European Patent 0 211 166, which have a stiff electrode surface which is also parallel to the electrode catheter. The electrode surface would not come into contact with tissue if it were rearranged to a position in an attempt to have the helix coiled around an axis parallel to the electrode catheter. Moreover, if the position of the fixed helix in the latter electrode devices were attempted to be changed so as to dispose the helix at a right angle to the electrode surface, further design problems would arise. By contrast, in the electrode arrangement in accordance with the invention disclosed herein, the fixing element can be advanced parallel to the electrode catheter even if the electrode surface is also parallel to the electrode catheter, since the flexibility of the electrode makes it possible first to affix the electrode using the fixing element in the correct position at the extreme distal end of the electrode, and then to bend the electrode against the tissue, with the electrode possibly being sutured in this configuration. Moreover, if two electrodes are to be utilized, for example for stimulating a heart, the electrodes can be configures so that they substantially enclose the heart, and a fixing element can be provided at one end of each of the electrodes, with the opposite ends of the electrodes being mechanically and electrically connected at the electrode catheters, thereby affixing electrodes to the heart with no need to suture the electrodes to the heart.

In a further embodiment of the electrode arrangement in accordance with the principles of the present invention, the electrode is formed by a thin, flexible and electrically insulated electrode carrier, on which at least one coiled conductor is arranged in a predetermined pattern, with a portion of the coil conductor being exposed to form the electrode surface. A tubular element is attached to the electrode carrier as an extension of the electrode catheter, with the fixing device located at the free (distal) end of the tubular element.

The tubular element enables the stylet to stabilize the flexible electrode during introduction thereof, with no risk of damage to any other tissue, which would otherwise be a risk if the stylet were unshielded. Additionally, the stylet acts directly on the fixing device. Placement of the fixing device at the end of the tubular element affixes the extreme distal end of the electrode to the tissue. This is an advantage when the fixing element is advanced parallel to the electrode catheter, because the actual penetration of tissue is facilitated if the fixing element can also be pressed against the tissue.

It is also possible to provide another fixing device located at the opposite end of the tubular element. Both ends of the electrode can then be affixed to tissue using the stylet, which is a particular advantage since there is a shortage of space around the tissue to which the electrode is to be affixed. The entire fixing procedure can then be controlled from outside the body of the patient.

In a further embodiment of the electrode arrangement of the invention, the fixing element is formed by a helix, the direction of movement of the helix forming an acute angle relative to the electrode plane. This is advantageous because the electrode is introduced parallel to the tissue. The acute angle must be sufficiently large for the fixing element to seat in the tissue when advanced, but not so large as to render the stylet incapable, by itself, of manipulating the fixation element. The angle is preferably less than 15° so as to minimize impact on the tissue.

Alternatively, the fixation element may be formed by a hook which is eccentrically rotatable around an axis parallel to the plane of the electrode surface. Rotation of this hook around the axis using the stylet causes the hook to emerge from the plane of the electrode surface, due to the eccentric rotation, and into the tissue against which the electrode is pressing.

DESCRIPTION OF THE PREFERRED EMBODIMENTS

Figure 1:
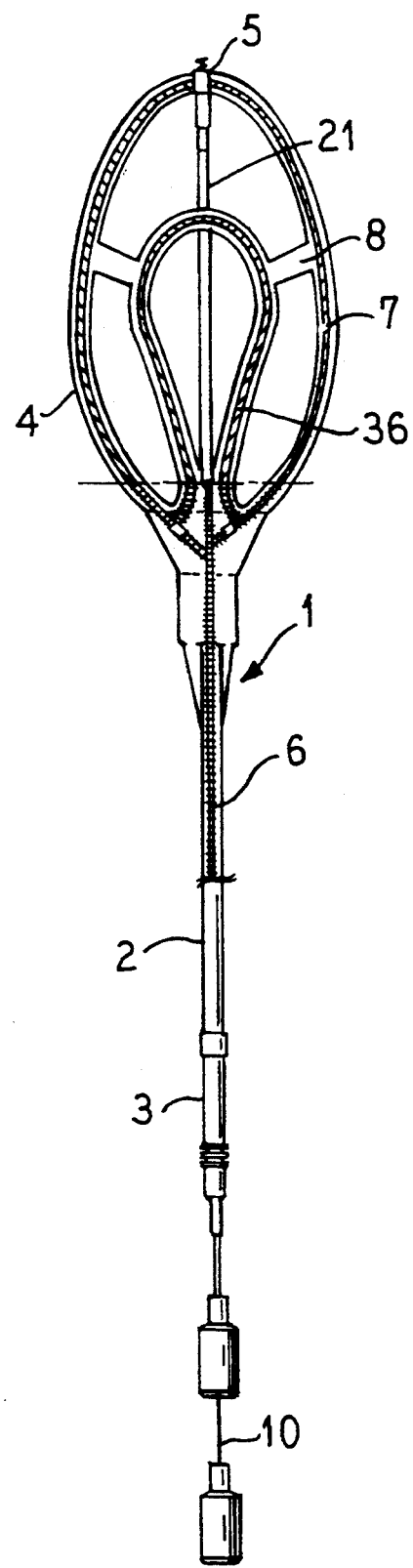
FIG. 1 is a plan view of an electrode arrangement constructed in accordance with the principles of the present invention, in a first embodiment.

The electrode arrangement 1 shown in FIG. 1 includes an electrode catheter 2, a connection contact (jack) 3, an electrode 4 and a fixing device 5. The connection contact 3, intended for coupling the electrode arrangement 1 to a stimulation pulse generator (not shown) such as a defibrillator, is electrically and mechanically coupled to the electrode catheter 2. A coiled electrode lead 6 passes from the connection contact 3 through the electrode catheter 2. Two coiled electrode conductors 7 and 36 are electrically connected to the electrode lead 6, and are arranged in a pattern on a thin, flexible and electrically insulating electrode carrier 8 within the electrode 4. The electrode catheter 2 has a channel extending therethrough into which a styler 10 can be introduced to control the fixing device 5. An insulated, coiled electrode conductor 21, arranged as an extension of the electrode lead 6 to the fixing device 5, is disposed on the electrode carrier 8. The stylet 10 runs inside the insulated electrode conductor 21 and removably mechanically engages the fixing device 5, so the stylet 10 can be removed after implantation. The electrode conductor 21 may alternatively be uninsulated, so as to form a part of the active electrode surface defined by exposed portions of the coiled electrode conductors 7 and 36.

Figure 2:
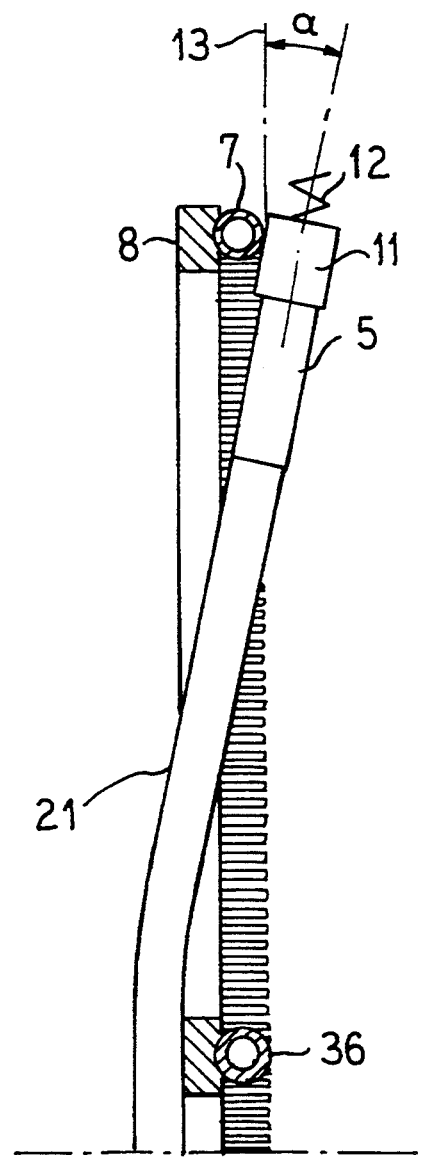
FIG. 2 shows an enlarged view of the fixing device in the embodiment of the electrode arrangement of FIG. 1.

As shown in FIG. 2, the fixing device 5 has a sleeve 11 and a helix 12. The helix 12 is screwed in and out of the sleeve 11 using the stylet 10. The direction of movement of the helix 12 follows a line which forms an acute angle α with the plane 13 of the electrode surface. The angle α is formed by the insulated electrode conductor 21, which runs atop the electrode carrier 5 when crossing the second electrode conductor 36, and running under the plane 13 of the electrode surface when it reaches the first electrode conductor 7. As a consequence of the angle α, the helix 12 emerges from the plane 13 of the electrode surface when screwed out of the sleeve 11, thereby seating itself in tissue, for example, in the pericardium around a heart. Since only pericardium is used for attaching the electrode arrangement to the heart, there is no damage to the epicardium. In addition, the pericardium remains generally intact, so that its function of protecting the heart is uncompromised.

If the initially selected placement of the electrode 4 during implantation proves to be unsuitable, the helix 12 can simply be retracted back into the sleeve 11 with the stylet 10. The electrode 4 can then be moved to another part of the heart and affixed at that location.

Depending on the tissue to be stimulated, and where the electrode device is to be situated to maximize stimulation efficacy, the angle α and the length of the helix 12 can vary. If tissue to be stimulated is sensitive, and there is less sensitive tissue nearby, the electrode arrangement 1 can be seated in the less sensitive tissue. Placement of the fixing device 5 does not have to be at the free end of the further electrode conductor 21, but can be at other locations.

Figure 3A:
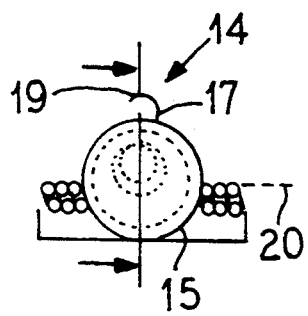
FIG. 3 is an enlarged view of an alternative version of a fixing device constructed in accordance with the principles of the present invention.
Figure 3B:
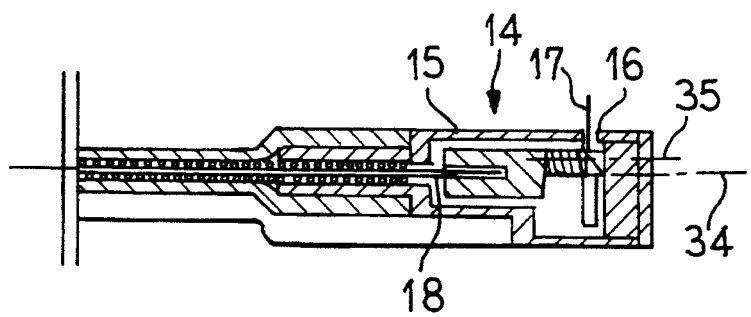

An alternative fixing device 14 is shown in FIG. 3, having a sleeve 15 with a groove 16 in a surface thereof and an eccentrically rotatable hook 17, which is disposed around the center axis 34 of the sleeve 15. The rotational axis 35 of the hook 17 is offset relative to the center axis 34 of the sleeve 15 to produce the eccentricity. When the hook 17 is rotated by the action of a stylet 18, the pointed end 19 of the hook 17 advances downwardly below the plane 20 of the electrode surface, and into underlying tissue, for example, pericardium tissue around the heart. The hook 17 can simply be retracted back into the sleeve 15 if the electrode 4 needs to be relocated.

As the fixing device 5 in FIG. 2, the fixing device 14 shown in FIG. 3 can be located anywhere along the longitudinal axis of the electrode 4. The sleeve 15 and the hook 17 can be designed so that the hook 17 affixes the electrode 4 to tissue on the passive side of the electrode 4.

Figure 4:
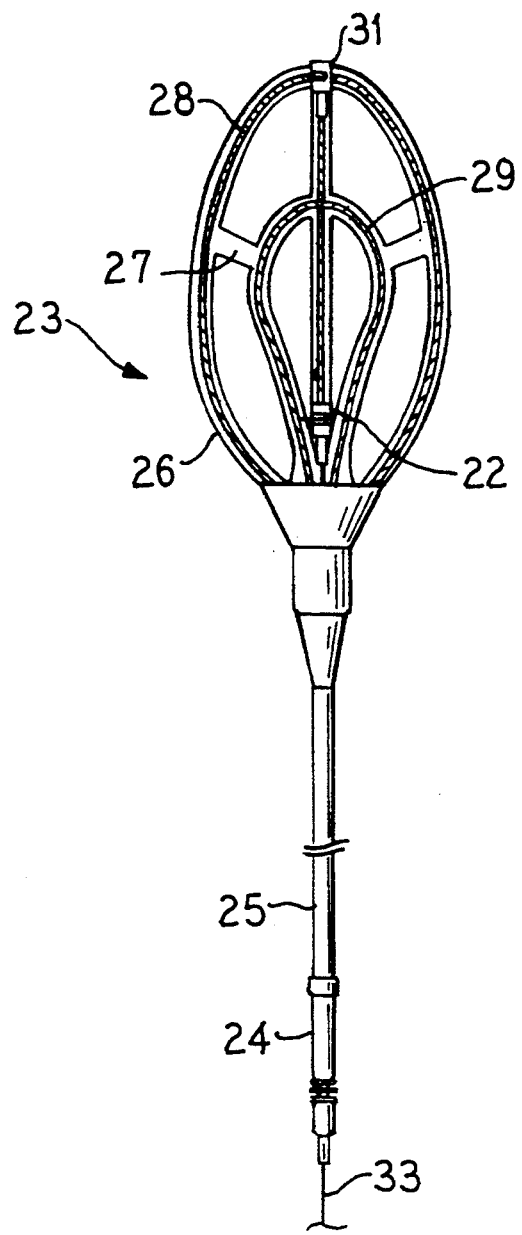
FIG. 4 is a plan view of an electrode arrangement constructed in accordance with the principles of the present invention, in a second embodiment.

A second embodiment of an electrode arrangement 23 is shown in FIG. 4. In principle, the electrode arrangement 23 is constructed in the same manner as the electrode arrangement 1 in the embodiment of FIG. 1, with a connection contact 24 for coupling the electrode arrangement 23 to a stimulation pulse generator (not shown), such as a defibrillator, an electrode catheter 25 coupled at one end to the connection contact 24, and coupled to an electrode 26 at the other end. The electrode 26 has a thin, flexible electrode carrier 27, on which a first coiled conductor 28 is arranged along the periphery of the electrode carrier 27, and a second coiled conductor 29 is looped inside the first conductor 28. The first and second conductors 28 have exposed portions which form the electrode surface. An electrode lead (not shown) is provided inside the electrode catheter 25 for electrically connecting connection contact 24 to the first and second conductors 28 and 29, in the same manner as shown in FIG. 1. A first fixing device 31 is located at the free (distal) end of the electrode carrier 27, and a second fixing device 22 is located at its opposite end. A tubular element 32 is provided between the two fixing devices 22 and 31. The two fixing devices 22 and 31 are constructed as shown in FIG. 3 and are manipulated with a stylet 33. With the two fixing devices 22 and 31, the two ends of the electrode 26 can be affixed with an optional orientation to the tissue which is to be stimulated. Surgery can thereby be minimized, since the procedure for affixing the electrode to tissue is controlled from outside the body of the patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical electrode arrangement for in vivo delivery of electrical energy to tissue, comprising:
   a catheter containing an electrical lead and having a channel therein;
   a thin, flexible, planar electrode having at least one partially exposed electrically conductive element therein electrically connected to said lead and defining a broad electrode surface; and
   fixing means for attaching said electrode to tissue including a fixing element adapted to penetrate said tissue and mounted on said electrode for movement independently of said electrode, and stylet means, receivable in said channel of said catheter and releasably mechanically engageable with said fixing element, for moving said fixing element between a retracted position and an advanced position wherein said fixing element protrudes from said electrode surface.

2. An electrode arrangement as claimed in claim 1 wherein said electrode further includes a thin, flexible electrode carrier consisting of electrically insulating material, and wherein said at least one electrically conductive element comprises at least one coiled conductor arranged in a predetermined pattern on said electrode carrier to form said electrode surface, and said electrode arrangement further comprising a tubular element having a first end attached to said electrode carrier and an opposite free end, said tubular element forming an extension of said catheter with said stylet means being receivable in said tubular element and said fixing means being disposed at said free end of said tubular element.

3. An electrode arrangement as claimed in claim 2 further comprising at least one additional fixing means having a fixing element releasably mechanically engageable with said stylet means and disposed at said first end of said tubular element.

4. An electrode arrangement as claimed in claim 1 wherein said fixing element consists of a helix with a pointed tip, said helix being mounted on said electrode for rotation by said stylet means around a rotational axis along which said helix is advanced by said stylet means, said rotational axis forming an acute angle relative to a plane containing said electrode surface.

5. An electrode arrangement as claimed in claim 4 wherein said acute angle is less than 15°.

6. An electrode arrangement as claimed in claim 1 wherein said fixing element consists of a hook mounted on said electrode for eccentric rotation around an axis which is parallel to a plane containing said electrode surface.

7. A medical electrode arrangement for in vivo delivery of electrical energy to tissue, for use with a stylet, comprising:
   a catheter containing an electrical lead and having a channel therein of a size adapted to receive said stylet;
   a thin, flexible, planar electrode having at least one partially exposed electrically conductive element therein electrically connected to said lead and defining a broad electrode surface; and
   fixing means for attaching said electrode to tissue including a fixing element adapted to penetrate said tissue and mounted on said electrode for movement independently of said electrode, and adapted for releasable mechanical engagement with said stylet, when received in said channel of said catheter, said fixing means when engaged with said stylet being movable between a retracted position and an advanced position wherein said fixing element protrudes from said electrode surface.

8. An electrode arrangement as claimed in claim 7 wherein said electrode further includes a thin, flexible electrode carrier consisting of electrically insulating material and wherein said at least one electrically conductive element comprises at least one coiled conductor arranged in a predetermined pattern on said electrode carrier to form said electrode surface, said electrode arrangement further comprising a tubular element having a first end attached to said electrode carrier and an opposite free end, said tubular element forming an extension of said catheter and having a size adapted for receiving said stylet therein, said fixing means being disposed at said free end of said tubular element.

9. An electrode arrangement as claimed in claim 8 further comprising at least one additional fixing means having a fixing element adapted for releasable mechanical engagement with said stylet and disposed at said first end of said tubular element.

10. An electrode arrangement as claimed in claim 7 wherein said fixing element consists of a helix with a pointed tip, said helix being mounted on said electrode so as to be rotatable by said stylet around a rotational axis along which said helix is advanced by said stylet, said rotational axis forming an acute angle relative to a plane containing said electrode surface.

11. An electrode arrangement as claimed in claim 10 wherein said acute angle is less than 15°.

12. An electrode arrangement as claimed in claim 7 wherein said fixing element consists of a hook mounted on said electrode for eccentric rotation around an axis which is parallel to a plane containing said electrode surface.

* * * * *